United States Patent
Watanabe et al.

(10) Patent No.: US 9,668,707 B2
(45) Date of Patent: Jun. 6, 2017

(54) MOBILE RADIATION IMAGING APPARATUS, METHOD FOR CONTROLLING MOBILE RADIATION IMAGING APPARATUS, AND STORAGE MEDIUM

(71) Applicant: CANON KABUSHIKI KAISHA, Tokyo (JP)

(72) Inventors: Tetsuo Watanabe, Utsunomiya (JP); Katsushi Kato, Kawasaki (JP); Kensuke Kobayashi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 17 days.

(21) Appl. No.: 14/180,850

(22) Filed: Feb. 14, 2014

(65) Prior Publication Data
US 2014/0264061 A1    Sep. 18, 2014

(30) Foreign Application Priority Data
Mar. 14, 2013    (JP) ................................ 2013-051136

(51) Int. Cl.
*A61B 6/12* (2006.01)
*H04W 48/04* (2009.01)
*A61B 6/00* (2006.01)

(52) U.S. Cl.
CPC ............ *A61B 6/4405* (2013.01); *A61B 6/547* (2013.01); *A61B 6/56* (2013.01); *H04W 48/04* (2013.01)

(58) Field of Classification Search
CPC .......... A61B 6/4405; A61B 6/547; A61B 6/56
See application file for complete search history.

(56) References Cited

U.S. PATENT DOCUMENTS

| | | | |
|---|---|---|---|
| 7,104,686 B2 | 9/2006 | Watanabe et al. | 378/189 |
| 7,889,843 B2 | 2/2011 | Watanabe | 378/116 |
| 7,924,982 B2 | 4/2011 | Watanabe | 378/114 |
| 8,160,207 B2 | 4/2012 | Watanabe | 378/154 |
| 8,401,150 B2 | 3/2013 | Watanabe | 378/114 |

(Continued)

FOREIGN PATENT DOCUMENTS

JP    11-099144    4/1999

OTHER PUBLICATIONS

JIS Z 4905 (Japanese Industrial Standard "Photography—Medical radiographic cassetteslscreenslfilms and hard-copy imaging films—Dimensions and specifications"), in translation (Mar. 25, 2005).

*Primary Examiner* — David Porta
*Assistant Examiner* — Jeremy S Valentiner
(74) *Attorney, Agent, or Firm* — Fitzpatrick, Cella, Harper & Scinto

(57) ABSTRACT

A mobile radiation imaging apparatus includes: an irradiation unit that emits radiation; a moving unit that moves with the irradiation unit; an imaging unit that takes an image of an object irradiated with radiation and is able to transmit the image via the wireless communication or the wired communication; an obtaining unit that obtains information indicating in which area the moving unit is located among a wired communication area, a wirelessly communicable area, and a switching area for switching between the wireless communication and the wired communication; and a control unit that switches the communication with the imaging unit depending on the obtained information.

17 Claims, 8 Drawing Sheets

(56) References Cited

U.S. PATENT DOCUMENTS

| | | | |
|---|---|---|---|
| 8,723,131 B2 | 5/2014 | Kobayashi | 250/370.09 |
| 2006/0120512 A1* | 6/2006 | Watanabe | 378/198 |
| 2006/0280381 A1* | 12/2006 | Iwakiri | G01T 7/00 |
| | | | 382/305 |
| 2007/0153980 A1* | 7/2007 | Butzine | 378/198 |
| 2008/0161672 A1* | 7/2008 | Marar | A61B 5/055 |
| | | | 600/407 |
| 2009/0186633 A1* | 7/2009 | Yonker | 455/456.6 |
| 2010/0019720 A1* | 1/2010 | Liu | A61B 6/4233 |
| | | | 320/107 |
| 2010/0034356 A1* | 2/2010 | Hayashida | 378/98 |
| 2010/0169423 A1* | 7/2010 | Eguchi | A61B 6/4233 |
| | | | 709/204 |
| 2010/0202589 A1* | 8/2010 | Ohta | A61B 6/4233 |
| | | | 378/98 |
| 2011/0238343 A1* | 9/2011 | Kamiya | A61B 6/4494 |
| | | | 702/63 |
| 2011/0284700 A1* | 11/2011 | Brand | B61L 15/0036 |
| | | | 246/28 R |
| 2012/0051521 A1* | 3/2012 | Nishino | A61B 6/4405 |
| | | | 378/98.5 |
| 2012/0273688 A1* | 11/2012 | Tsai | G01T 7/00 |
| | | | 250/370.07 |
| 2013/0058455 A1* | 3/2013 | Kuwabara | A61B 6/4283 |
| | | | 378/62 |
| 2013/0064351 A1* | 3/2013 | Urbon | A61B 6/4405 |
| | | | 378/98.5 |
| 2013/0195251 A1* | 8/2013 | Saigusa | H05G 1/30 |
| | | | 378/101 |
| 2014/0016747 A1 | 1/2014 | Watanabe | 378/62 |

\* cited by examiner

F I G. 3
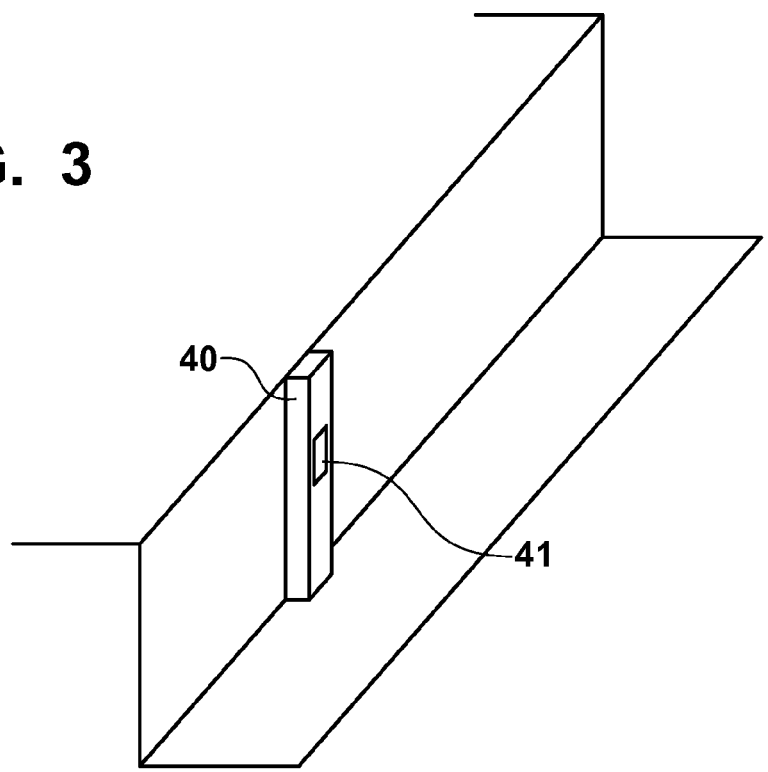
F I G. 4
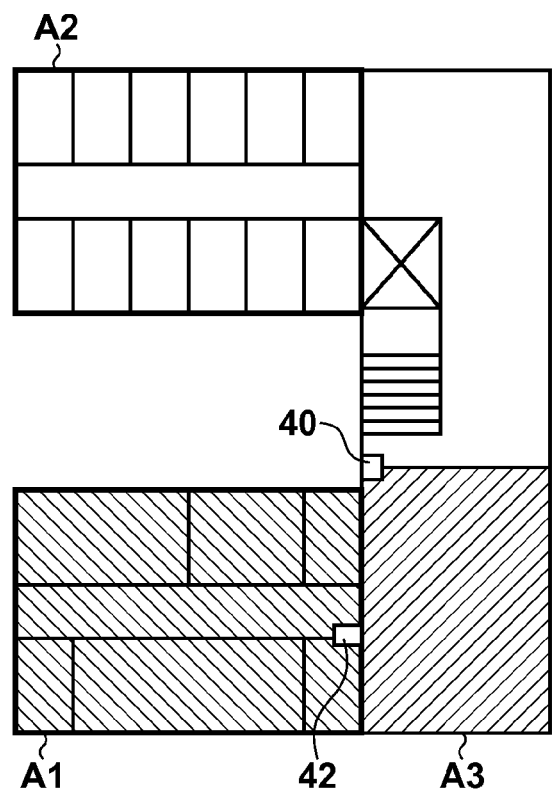

F I G. 6
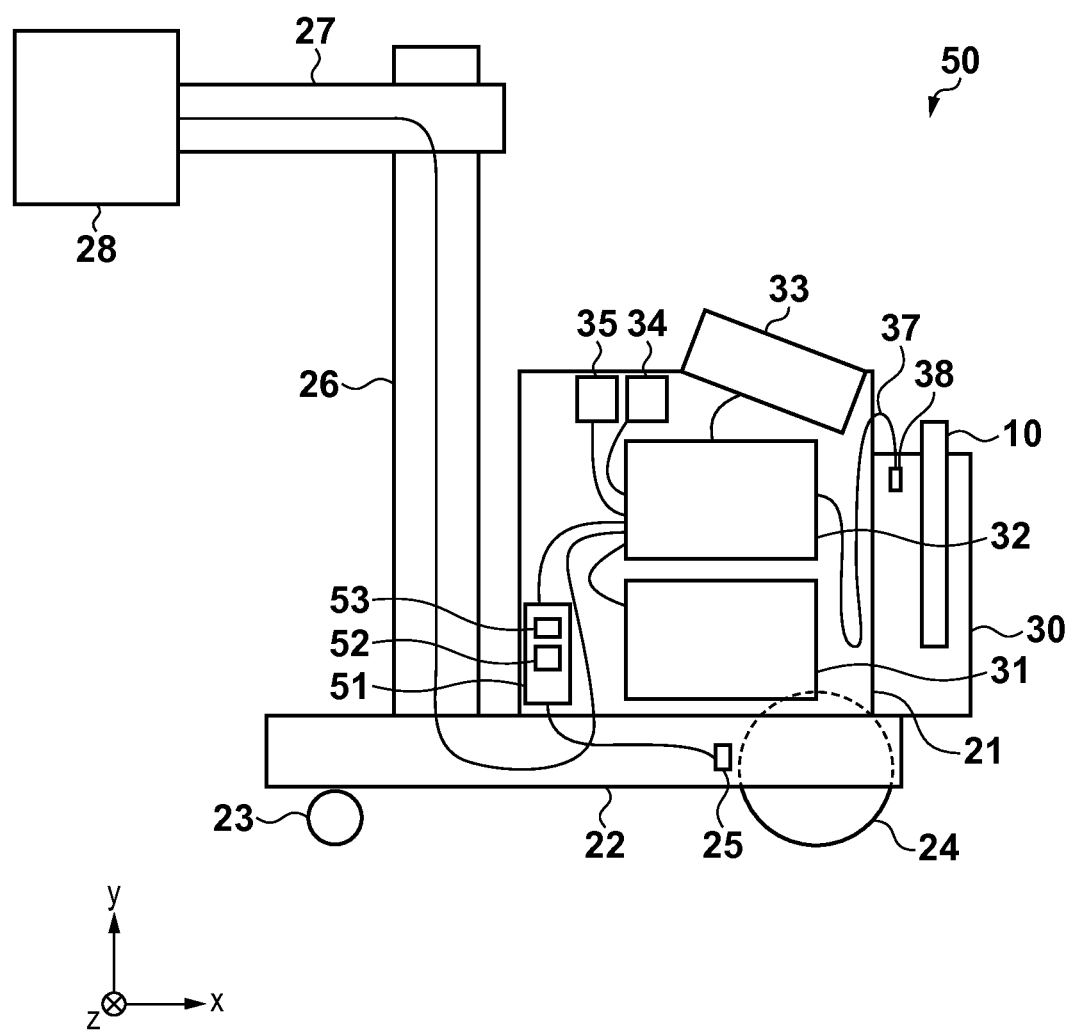

F I G. 8
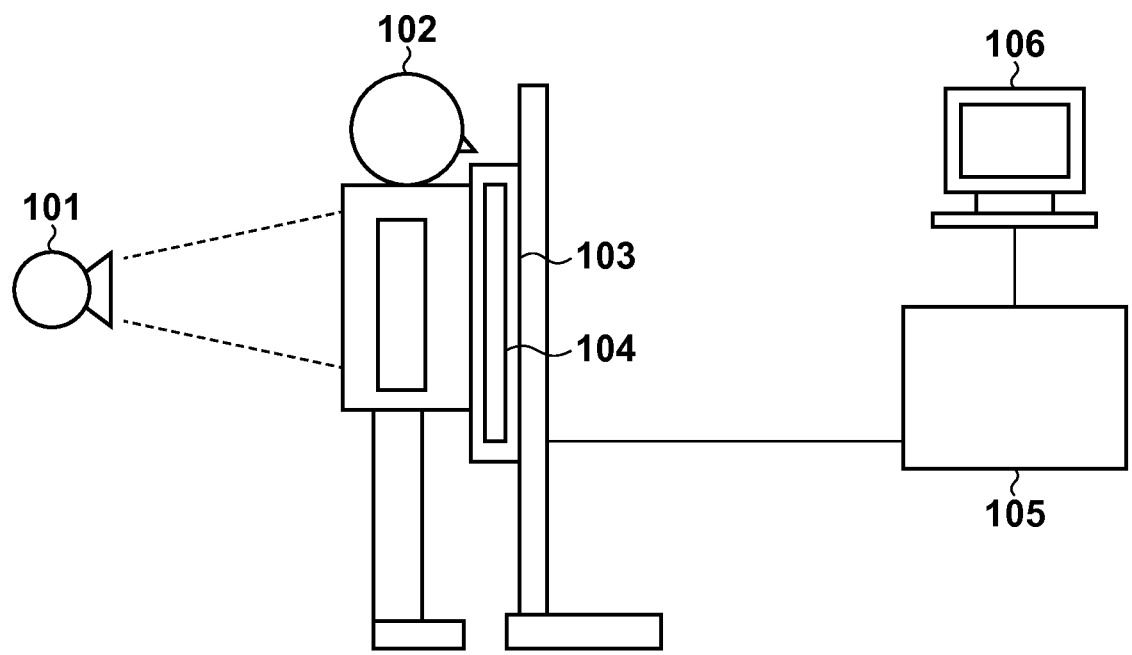

MOBILE RADIATION IMAGING APPARATUS, METHOD FOR CONTROLLING MOBILE RADIATION IMAGING APPARATUS, AND STORAGE MEDIUM

BACKGROUND OF THE INVENTION

Field of the Invention

The present invention relates to a mobile radiation imaging apparatus, a method for controlling the mobile radiation imaging apparatus, and a storage medium.

Description of the Related Art

Conventionally, apparatuses for obtaining a radiation image by irradiating an object with radiation, and detecting intensity distribution of the radiation transmitted through the object are universally used in the fields of industrial non-destructive inspection or medical diagnosis. Common methods of such imaging include a film-screen method and a CR method. In the methods, a photographic sensitive film or a fluorescent substance plate in which an image is accumulated as a latent image is put into a storage case that is called a cassette standardized in Non-Patent Document 1 (JIS Z 4905), and is used to take an image.

Meanwhile, with recent advancement in digital technology, methods for obtaining a radiation image with a high image quality by converting a radiation image into an electric signal, subjecting this electric signal to image processing, and then reproducing the processed electric signal as a visible image on a CRT or the like have spread.

FIG. 8 is a schematic diagram illustrating a conventional system using a radiation imaging apparatus. A radiation imaging apparatus 103 includes a radiation detection sensor 104 built therein. An object 102 is irradiated with radiation generated by a radiation generating apparatus 101, and the radiation detection sensor 104 (detection unit) converts the radiation transmitted through the object into visible light via a fluorescent substance, and detects the visible light as an electric signal with the use of photoelectric conversion elements arranged in a two-dimensional grid. A control unit 105 that controls this detection unit to perform read-out driving or image transfer is provided. The control unit 105 performs digital image processing on an image output from the detection unit, and displays the radiation image of the object on a monitor 106. This system has an advantage in being able to monitor the image in real time, in contrast to the previously-described radiation image storing and reproducing system in which the image is read out by post-processing. This imaging system includes a detection panel for the radiation detection sensor 104 on a special trestle that is configured depending on whether an image is taken in the upright position, the supine position, or the like, and the appropriate trestle is used depending on the need.

Conventionally, this type of radiation imaging apparatus is installed and used in a radiation room. In recent years, however, a portable thin and light imaging apparatus (referred to as "electronic cassette") has been developed in order to enable faster imaging of a wider range of site. As a result, an imaging system has been proposed that is applicable to cassette-based imaging not only in a radiation room but also during a doctor's round (Japanese Patent Laid-Open No. 11-99144).

In recent years, wireless communication become widespread as a communication method of an electronic cassette, and such an electronic cassette is widely used due to its advantages in operability without a communication cable. However, this electronic cassette is relatively less likely to maintain reliable communication and the effect of radiated electromagnetic wave is significant, as compared with a conventional electronic cassette of wired cable type, and thus proper management is required. In the case of a general radiation room, wireless environment such as channel setting can be optimized according to the place where the electronic cassette is installed. However, in the case of a doctor's round, due to the mobility of the electronic cassette, the environment thereof varies depending on the destination, and thus it is more difficult to establish reliable communication. Particularly, in an area in which a device sensitive and susceptible to an electromagnetic wave is disposed, it is sometimes necessary to restrict the use of a wireless network itself.

SUMMARY OF THE INVENTION

The present invention provides a technology for making communication with an imaging unit switchable, based on information indicating in which area a mobile radiation imaging apparatus is located among a wired communication area, a wirelessly communicable area, and a switching area for switching between wireless and wired communication.

According to one aspect of the present invention, there is provided a mobile radiation imaging apparatus having an irradiation unit configured to emit radiation, and a moving unit configured to move with the irradiation unit, the mobile radiation imaging apparatus comprising: an imaging unit configured to take an image of an object irradiated with radiation, and is capable of transmitting the image via wireless communication or wired communication; an obtaining unit configured to obtain information indicating in which area the moving unit is located among a wired communication area, a wirelessly communicable area, and a switching area for switching between the wireless communication and the wired communication; and a control unit configured to switch the communication with the imaging unit depending on the obtained information.

According to another aspect of the present invention, there is provided a mobile radiation imaging apparatus having an irradiation unit configured to emit radiation, and a moving unit configured to move with the irradiation unit, the mobile radiation imaging apparatus comprising: an imaging unit configured to take an image of an object irradiated with radiation, and is capable of transmitting the image via wireless communication or wired communication; an obtaining unit configured to obtain position information of the mobile radiation imaging apparatus; and a control unit configured to switch the communication with the imaging unit based on the obtained position information.

Further features of the present invention will become apparent from the following description of exemplary embodiments (with reference to the attached drawings).

BRIEF DESCRIPTION OF THE DRAWINGS

FIG. 3 is a diagram illustrating exemplified installation of a transmitting unit for transmitting an area switching signal.

FIG. 4 is a diagram illustrating an exemplified layout of areas in which the mobile imaging apparatus can move.

FIG. 6 is a diagram illustrating a configuration of a mobile imaging apparatus according to a second embodiment.

FIG. 8 is a diagram illustrating a conventional system using a radiation imaging apparatus.

DESCRIPTION OF THE EMBODIMENTS

Hereinafter, a mobile radiation imaging apparatus and a method for controlling the mobile radiation imaging apparatus according to embodiments will be described with reference to the drawings. However, constituent components described in the embodiments are merely examples, and the technical scope of the present invention is not limited to the following individual embodiments but is defined by the scope of claims.

Note that, although the following embodiments describe mobile radiation imaging apparatuses for medical use that image a human body as an object using radiation, the idea of the present invention is not limited to this example and the present invention is also applicable to a radiation imaging apparatus that images another object.

First Embodiment

Figure 1:
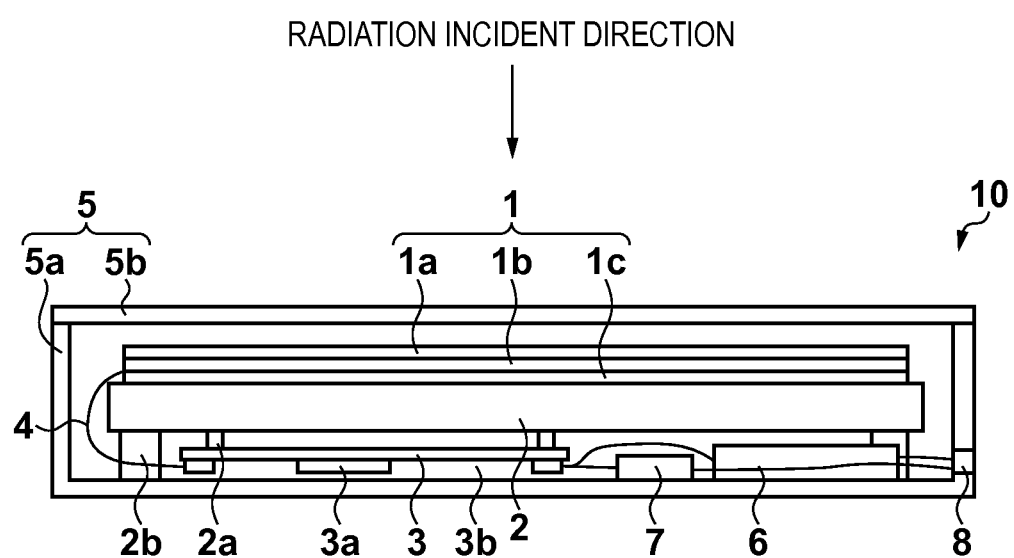
FIG. 1 is a transverse sectional view illustrating an imaging unit of a mobile imaging apparatus according to a first embodiment.
Figure 2:
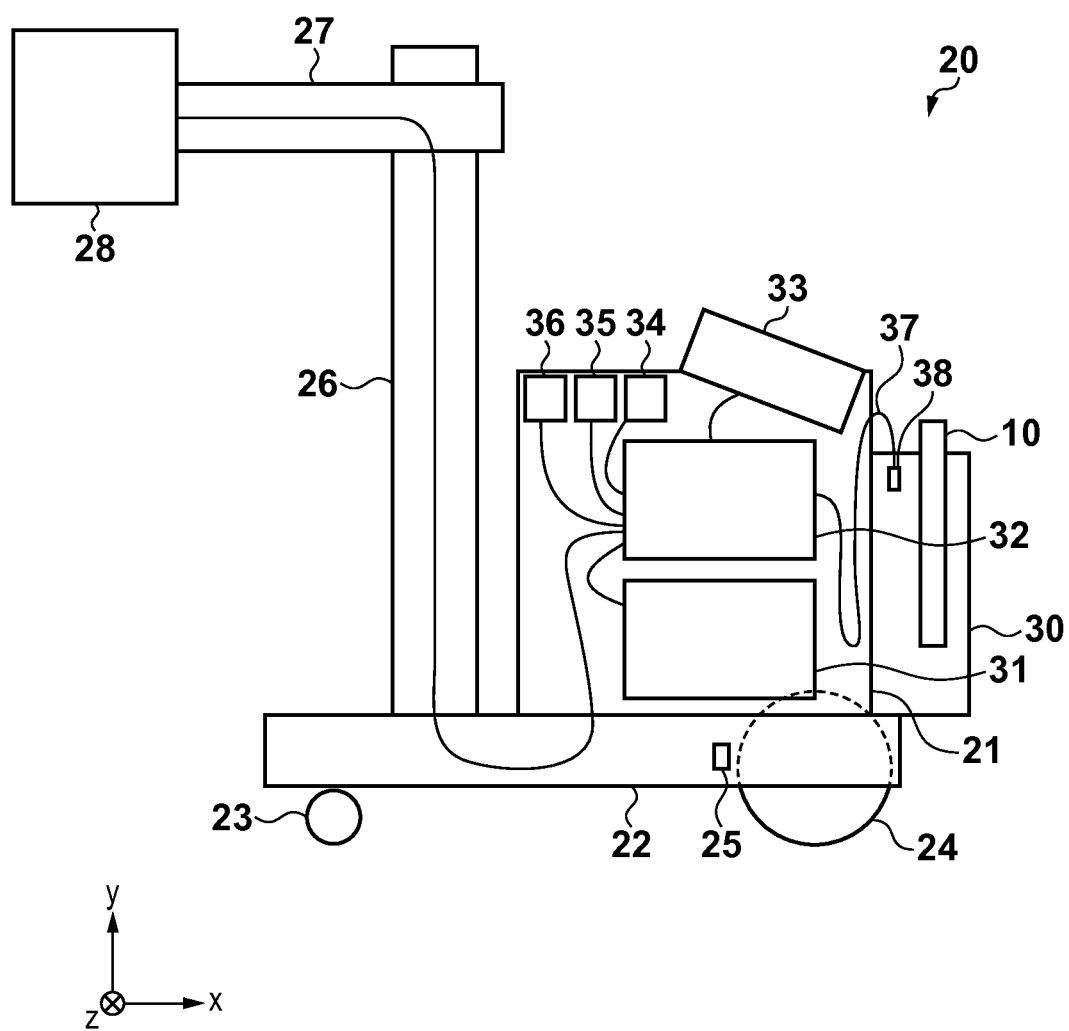
FIG. 2 is a diagram illustrating a configuration of the mobile imaging apparatus according to the first embodiment.

FIG. 1 is a transverse sectional view illustrating an imaging unit of a mobile radiation imaging apparatus (hereinafter, referred to also as "mobile imaging apparatus") according to the present embodiment, and FIG. 2 is a diagram illustrating a configuration of the mobile imaging apparatus. FIGS. 3 to 5 are diagrams illustrating use of the mobile imaging apparatus and a method for controlling thereof.

In FIG. 1, a radiation image detection panel 1 is constituted by a fluorescent plate 1a, photoelectric conversion elements 1b, and a base substrate 1c. A glass plate is often used as the base substrate 1c due to its advantages of not causing a chemical action with a semiconductor element, of being able to withstand the temperature during a semiconductor process, and in requirements for dimensional stability and the like. The photoelectric conversion elements 1b are formed in a two dimensional array on such a glass substrate by a semiconductor process. The fluorescent plate 1a is obtained by applying a fluorescent substance of a metallic compound to a resin plate, and is formed in one piece with the base substrate 1c by adhesion.

These components serving as the radiation image detection panel 1 are fixed to and are supported by a metallic base 2, thereby ensuring mechanical strength. An electronic component 3a for processing an electric signal converted by the photoelectric conversion element 1b is mounted on a circuit board 3. The circuit board 3 is connected to the photoelectric conversion element 1b by a flexible circuit board 4, and is fixed to projections 2a provided on the rear face (that is opposite to the face which the radiation image detection panel 1 is fixed to and supported on) of the base 2. The base 2 is fixed to a chassis body 5a via supporting sections 2b, and is sealed by a radiation transmissive chassis cover 5b, thereby constituting an imaging unit 10 serving as an electronic cassette.

The imaging unit 10 also includes a battery 6 that supplies electric power to the circuit board 3 and the like, and a communication unit 7 that transmit signals such as an image signal and a control signal. When the imaging unit 10 is used in a wireless state, the battery 6 performs power feeding and communication is performed using a wireless communication function of the communication unit 7. In the case where a wired cable is used instead of wireless connection, the cable is externally connected to a connector 8 formed in the chassis body 5a of the imaging unit 10. Power feeding and communication are performed directly by the cable, and thus running out of the battery and unreliable wireless communication are solved.

Such an imaging unit 10 is combined with a mobile radiation generating apparatus for use during a doctor's round, and is used in a mobile imaging apparatus 20 shown in FIG. 2. In FIG. 2, the mobile imaging apparatus 20 includes a plurality of wheels 23 and 24 on a bottom 22 of a main body 21 thereof, and is arbitrarily movable. The main body 21 includes a detection unit 25 for detecting rotation of either wheels 23 or 24, for example, the wheels 24, and has a function to determine the movement state of the mobile imaging apparatus 20 (whether it is at a stop or moving) using the detection result of the detection unit 25. This determination function can be realized by, for example, a rotary encoder and the like.

The main body 21 is provided with a vertical column 26 that is supported so as to be rotatable around an axis. An arm 27 is provided that extends in a horizontal direction with respect to the column 26 (in the x direction in FIG. 2) and is supported so as to be movable in the vertical direction along the column 26 (in the y direction in FIG. 2). At the front end of the arm 27, a radiation generating unit 28 is provided that includes a radiation tube and can move in the horizontal direction along the arm 27. The radiation generating unit 28 can be adjusted so as to perform irradiation in any direction.

The main body 21 is provided with an accommodation unit 30 for accommodating the imaging unit 10. The imaging unit 10 is accommodated in the accommodation unit 30 when the mobile imaging apparatus 20 is moving. The imaging unit 10 is removed from the accommodation unit 30 and is installed at a predetermined position, when the mobile imaging apparatus 20 is used (when capturing an image).

The main body 21 includes a control unit 32 for driving of a tube for emitting radiation, controlling a mobile apparatus, and controlling imaging by the imaging unit 10, and a battery 31 (power supply) for supplying required electric power to various types of units.

The control unit 32 includes a storage unit for storing information such as an image transmitted from the imaging unit 10, an interface for an operation for interlocking the radiation generating unit 28 and the imaging unit 10, and a power supply output control unit for controlling an output of the battery 31. The control unit 32 performs control of entire operations of the storage unit, the interface, and the power supply output control unit.

An input and output unit 33, which is used for operating the mobile imaging apparatus 20, is constituted by a monitor (display unit) for display output and an input device for inputting an operation of the apparatus, and is arranged in the upper portion of the main body 21. The input device may be, for example, buttons, a touch panel, or the like of selection keys for switching the selected position on the monitor.

The display unit displays an operation menu through which, for example, a site to be imaged is selected, the imaging unit 10 is shifted to a state in which imaging is possible, and imaging conditions such as a tube voltage or a tube current of the radiation generating unit 28, an irradiation time period, and the like are set. The items of the imaging conditions are selected using the input device to perform imaging. The input device can also be used to perform a series of operations from processing such as trimming or rotating on the image to storing the processed image in the storage unit of the control unit 32.

The control unit 32 also includes a management unit for managing information on a patient for whom imaging was instructed, an imaging condition, and an imaging history. This management unit can be configured by, for example, a software module that is incorporated into the control unit 32. An operator (technician) of the mobile imaging apparatus 20 can check a list of information on a patient (test object) and the like via the input and output unit 33. The information is operated by the apparatus communicating, via an external communication unit 34 connected to the control unit 32, with an external terminal within a hospital, or a server (information processing apparatus), a database, or the like that is located outside the hospital, for example.

A wireless communication unit 35, which communicates exclusively with the communication unit 7 built in the imaging unit 10, is used when an image is taken. The control unit 32 transmits an instruction to take an image in the imaging condition set using the input and output unit 33, the imaging unit 10 takes an image in synchronization with irradiation with radiation by the radiation generating unit 28, and data of the image is transmitted via wireless communication between the communication unit 7 and the wireless communication unit 35. The data of the image is stored in the storage unit (memory) of the control unit 32 and finally transferred to an external terminal.

On the other hand, in the case where data of the image taken by the imaging unit 10 is transmitted via wired communication instead of wireless communication, a cable 37 connected to the control unit 32 is used. By connecting a connector 38 at the front end of the cable 37 to the connector 8 of the imaging unit 10, it is possible to perform power feeding and communication using the cable.

As described above, the control unit 32 of the mobile imaging apparatus 20, which can be used by switching between wired and wireless communication, sets a wireless communication restricted area, and a switching area for switching between wired and wireless communication in the vicinity of the entrance of the wireless communication restricted area. The switching area is to appropriately perform switching from wireless communication to wired communication before the apparatus enters the wireless communication restricted area.

In the present embodiment, the main body 21 includes a receiving unit 36 that receives information for recognizing the switching area for switching between wireless and wired communication. The receiving unit 36 recognizes the switching area based on the information transmitted from an externally provided transmitting unit, and the control unit 32 prompts the operator to switch to wireless communication or wired communication, and executes processing relating to the switching of the communication in response to the operation of the operator. As shown in FIG. 3, for example, a gate 40 mounted on a side wall of the facility includes a transmitting unit 41 for transmitting a signal (area switching signal) for performing notification of the switching area. When the mobile imaging apparatus 20 has passed the gate 40, the receiving unit 36 receives a signal (area switching signal) from the transmitting unit 41. The control unit 32 recognizes that the mobile imaging apparatus 20 entered the switching area based on the reception result of the receiving unit 36, and prompts the operator (technician) to switch to wireless communication or wired communication.

For example, on a floor of a hospital in a layout as shown in FIG. 4, an area A1 indicated by hatching is a space in which a device susceptible to the effect of wireless communication is disposed, that is, an area in which wireless communication should be restricted (wired communication area). On the other hand, patient's bedrooms are in an area A2, which is an area in which wireless communication is possible for imaging during a doctor's round (wireless communication area). An area A3 provided between the area A1 and the area A2 serves as a communication switching area (wireless/wired switching area). Accordingly, a gate 42 as shown in FIG. 3 is arranged in the vicinity of the area entrance at the boundary between the area A1 and the area A3. Also, a gate 40 as shown in FIG. 3 is arranged in the vicinity of the area entrance at the boundary between the area A2 and the area A3. The respective gates 40 and 42 include the transmitting units 41 as shown in FIG. 3, and each transmitting unit transmits an area switching signal. If the receiving unit 36 of the mobile imaging apparatus 20 receives the area switching signal, the control unit 32 recognizes that the mobile imaging apparatus 20 has entered the switching area. The control unit 32 prompts the operator (technician) to switch to wireless communication or wired communication, and executes processing relating to the switching of the communication in response to the operation of the operator.

Figure 5A:
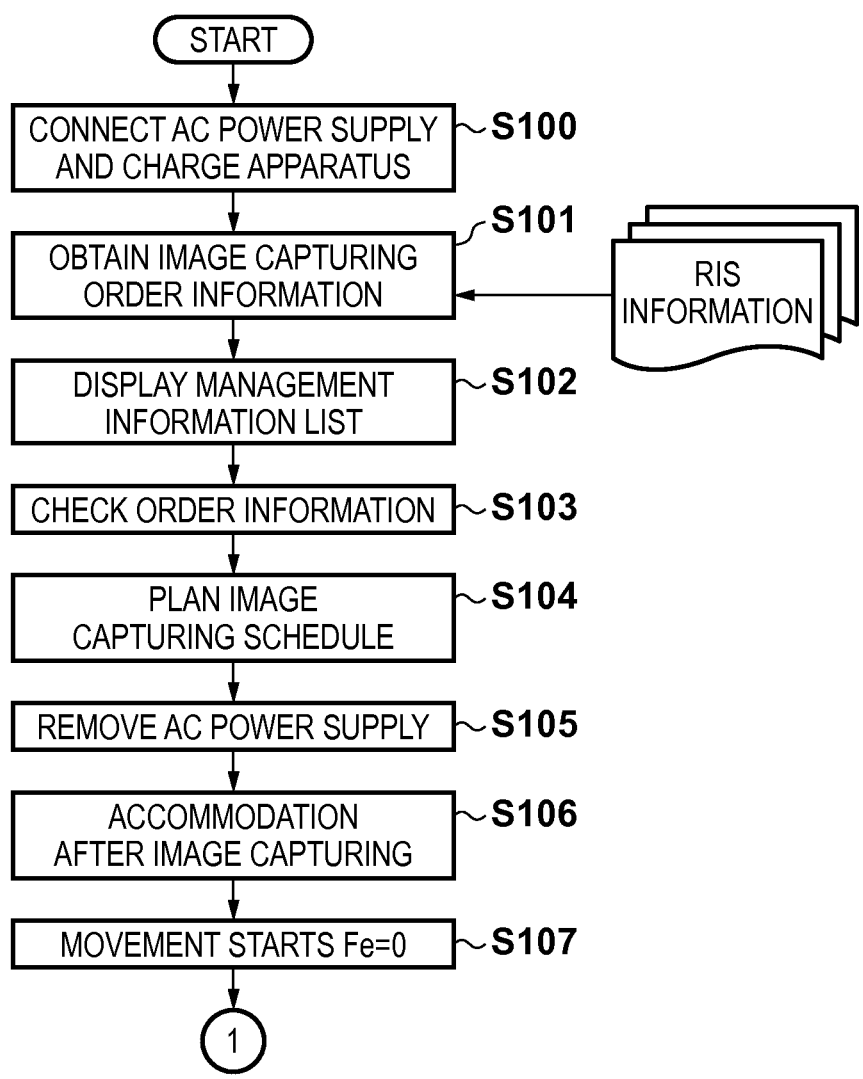
FIGS. 5A and 5B are diagrams illustrating a method for controlling the mobile imaging apparatus according to the first embodiment.
Figure 5B:
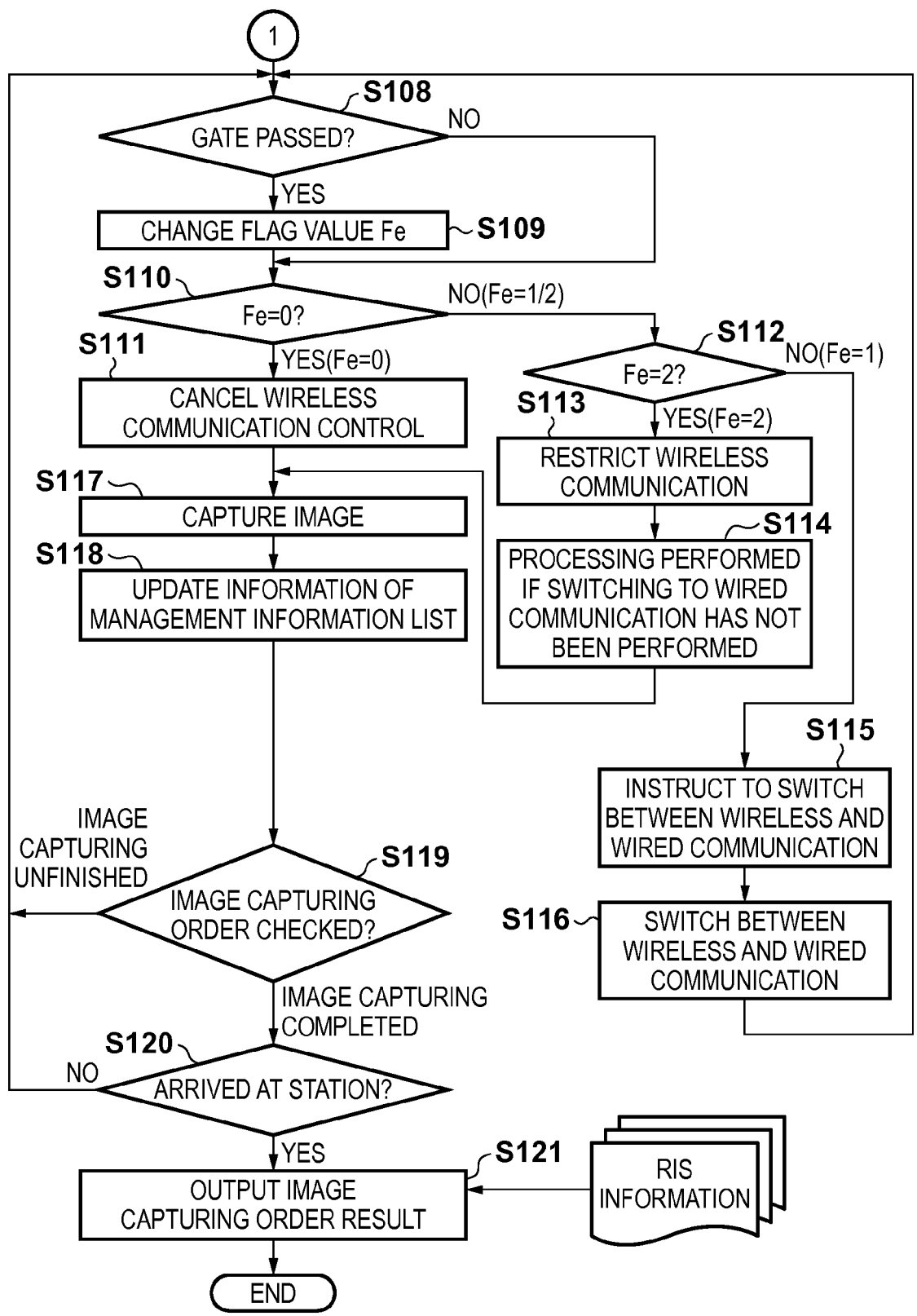

A workflow when the mobile imaging apparatus 20 is used is described with reference to FIGS. 5A and 5B. First, in step S100, as a preparatory state, an AC cable (not shown) for activating the mobile imaging apparatus 20 is connected to a commercial power supply, and the battery 31 is charged with electric power in advance.

In step S101, the control unit 32 obtains (uploads), for example, information on a patient for whom imaging was instructed or order information indicating an imaging condition from an RIS terminal within a hospital via the external communication unit 34.

In step S102, the uploaded order information is displayed in a list (a management information list) by the input and output unit 33, and in step S103, the operator (technician) checks the order information displayed in the list. The contents of the here displayed order information include, for example, information on a patient for whom imaging was instructed (e.g., patient information such as the name, sex, and the like, and the patient's bedroom number), and information indicating an imaging condition (e.g., the site to be imaged, the posture of the patient when being imaged, and the like).

In step S104, the technician plans a rough schedule of imaging during a doctor's round, taking into consideration the priority for imaging or the moving route. When the preparation is completed, the AC power supply is removed (S105), the imaging unit 10 is accommodated in the accommodation unit 30 (S106), and movement starts (S107). In step S107, the technician starts moving to a predetermined patient's bedroom in accordance with the planned schedule while pushing the mobile imaging apparatus 20.

The control unit 32 includes a calculation unit for managing a control flag Fe for identifying control areas. Here, the control areas include a wireless communication possible area (wirelessly communicable area), a wireless/wired switching area, and a wired connection area (area in which wireless communication should be restricted (wireless connection prohibited area)), and the values 0, 1, and 2 of the control flag Fe are assigned to the areas. In step S107, since the apparatus is in the wireless communication possible area, the value of the control flag Fe is set to "0".

The transmitting unit 41 of each gate transmits an area switching signal indicating the boundary between the corresponding areas. By analyzing to which value of the control flag Fe the area switching signal received by the receiving unit 36 corresponds, the control unit 32 can specify in which control area the mobile imaging apparatus 20 is moving.

In step S108, during the movement, the mobile imaging apparatus 20 monitors reception of the area switching signal by the receiving unit 36. If the receiving unit 36 has received the area switching signal, the control unit 32 determines that the apparatus has passed the gate. If the receiving unit 36 has not received the area switching signal, the control unit 32 determines that the apparatus has not passed the gate.

If it is determined in step S108 that the apparatus has passed the gate (Yes, in step S108), the procedure advances to step S109. In step S109, the area switching signal is transmitted to the control unit 32, and the calculation unit of the control unit 32 specifies a boundary between corresponding areas based on the area switching signal. For example, the transmitting unit 41 of the gate 40 transmits a signal for performing notification of the boundary between the wirelessly communicable area A2 (control flag Fe=0) and the wireless/wired switching area A3 (control flag Fe=1). Also, the transmitting unit 41 of the gate 42 transmits a signal for performing notification of the boundary between the wired communication area A1 (control flag Fe=2) and the wireless/wired switching area A3 (control flag Fe=1).

For example, when the mobile imaging apparatus 20 is in the area A2, the control flag Fe is set to "0". When the mobile imaging apparatus 20 has passed the gate 40 and moves from the area A2 to the area A3, the calculation unit of the control unit 32 changes the value "0" of the control flag Fe to "1". Also, when the mobile imaging apparatus 20 is in the area A3, the control flag Fe is set to "1". When the mobile imaging apparatus 20 has passed the gate 40 and moves from the area A3 to the area A2, the calculation unit of the control unit 32 changes the value "1" of the control flag Fe to "0".

Also, when the mobile imaging apparatus 20 is in the area A1, the control flag Fe is set to "2". When the mobile imaging apparatus 20 has passed the gate 42 and moves from the area A1 to the area A3, the calculation unit of the control unit 32 changes the value "2" of the control flag Fe to "1". Also, when the mobile imaging apparatus 20 is in the area A3, the control flag Fe is set to "1". When the mobile imaging apparatus 20 has passed the gate 42 and moves from the area A3 to the area A1, the calculation unit of the control unit 32 changes the value "1" of the control flag Fe to "2".

In step S110, the control unit 32 determines the value of the control flag Fe, and switches whether to use wireless communication or wired communication based on the value of the control flag Fe. If it is determined in step S110 that the value of the control flag Fe=0 (Yes, in step S110), the procedure advances to step S111, where the control unit 32 makes wireless communication between the wireless communication unit 35 and the communication unit 7 of the imaging unit 10 possible (wireless communication control is cancelled). Then, the procedure advances to step S117.

On the other hand, if it is determined in step S110 that the value of the control flag Fe 0, the procedure advances to step S112. If it is then determined in step S112 that the value of the control flag Fe=1 (No, in step S112), the procedure advances to step S115.

If the value of the control flag Fe is changed from "0" to "1", it means that the mobile imaging apparatus 20 is approaching the wired communication area. In this case, in step S115, the control unit 32 informs an operator of the approach of the apparatus to the area in which wireless communication should be restricted (wired communication area), and instructs the operator (technician) to switch to wired communication by displaying a message instructing the operator to switch, or alarming the operator by sound.

In step S116, the operator (technician) operates to switch from the wireless communication to wired communication in the area A3 in accordance with the instruction in step S115. The switching operation is performed by connecting the connector 38 of the cable 37 connected to the control unit 32 to the connector 8 of the imaging unit 10. When the control unit 32 detects that the wired cable 37 has been connected, the wireless communication is automatically switched to the wired communication. Accordingly, power feeding and image data communication are performed via the wired communication. The power supply output control unit of the control unit 32 controls an output of the battery 31 to switch from the wireless communication to wired communication. When the communication has been switched to the wired communication, electric power is fed to the imaging unit 10 from the battery 31 via the cable 37 under the control by the power supply output control unit.

The transmitting unit 41 of the gate 42 transmits the signal for performing notification of the boundary between the wired communication area A1 (control flag Fe=2) and the wireless/wired switching area A3 (control flag Fe=1). It is assumed, for example, that the mobile imaging apparatus 20 moves from the area A3 to the area A1, when the apparatus has passed the gate 42 (Yes, in step S108), the value of the control flag Fe is changed from "1" to "2" (step S109). If the determination result of step S110 shows that the value of the control flag Fe≠0, and the determination result of step S112 shows that the value of the control flag Fe=2, the procedure advances to step S113.

In step S113, the control unit 32 restricts wireless communication of image data between the wireless communication unit 35 and the communication unit 7 of the imaging unit 10 (wireless communication restriction). By the processing of this step, the wireless communication is restricted.

If the above-described operation in step S116 for switching the communication to the wired communication has not been performed when the apparatus has passed the gate 42, the control unit 32 performs, in step S114, processing performed if the switching from wireless to wired communication has not been performed. As the processing performed if the switching from wireless to wired communication has not been performed, the control unit 32 informs the operator (technician) of incompletion of switching to the wired connection, for example, by displaying the incompletion on the display unit or by alarming the operator by sound. If the mobile imaging apparatus 20 includes an electromagnetic braking device or an auxiliary electric-powered driving device, the control unit 32 controls suppression of braking by the braking device or driving by the auxiliary electric-powered driving device, and increases an operation load needed for movement. By increasing such an operation load, the processing for informing the operator (technician) that switching to the wired communication has not been completed.

Note that if the processing in step S116 has already been completed in the area A3, the control unit 32 skips this processing, and the procedure advances to step S117.

In step S117, imaging is performed. When the mobile imaging apparatus 20 arrives at a predetermined room in the area A2 or the area A1 and is stopped, the operator (technician) positions the radiation generating unit 28 at a predetermined imaging posture, then selects, on the display unit, a site to be imaged and sets the imaging condition such as the tube voltage and the mAS value of the radiation generating unit.

If the mobile imaging apparatus 20 is in the area A2, the image data is transmitted via the wireless communication between the communication unit 7 of the imaging unit 10 and the wireless communication unit 35, and the image data is stored in the storage unit of the control unit 32, and is finally transferred to an external terminal via the external communication unit 34. Also, if the mobile imaging apparatus 20 is in the area A1, the image data is transmitted to the control unit 32 via the cable 37, and is stored in the storage unit of the control unit 32.

In step S117, when the imaging of the patient (test object) is finished, the control unit 32 automatically updates, in step S118, information of the management information list relating to the corresponding patient (test object) as "imaging finished".

In step S119, the control unit 32 checks the imaging order information obtained in step S101. If there is an unfinished imaging order that is left (imaging unfinished), the operator moves the mobile imaging apparatus 20 to the room in which the next imaging is scheduled in order to perform imaging for the next patient (test object), and repeats the series of processing from step S108 onward.

Note that the above description was given taking an example of movement from the area A2 to the area A1 through the area A3, but in the case of movement from the area A1 to the area A2 through the area A3, processing that is opposite to the above-described processing may be performed when the apparatus has passed the gates 40 and 42.

When, finally, the imaging order information no longer includes an unfinished imaging order (imaging completed), the procedure advances to step S120. In step S120, when the mobile imaging apparatus 20 does not arrive at a waiting station (No, in step S120), the procedure returns to step S108, and a series of processing from step S108 onward is performed. When the mobile imaging apparatus 20 has arrived at the waiting station (Yes, in step S120), the image data stored in the storage unit (memory) of the data control unit 32 is output as an imaging order result (RIS information) that corresponds to the imaging order information, via the external communication unit 34. With the above-described steps, the imaging during a doctor's round ends. According to the present invention, it is possible to switch the communication with the imaging unit, based on the information indicating in which area the mobile radiation imaging apparatus is located among the wired communication area, the wirelessly communicable area, and the switching area for switching between wireless and wired communication. Therefore, it is possible to comply with the restriction of the wireless communication without the operator being conscious of it, and to suppress the effect of the wireless communication on other devices within a hospital.

Second Embodiment

Next, a mobile radiation imaging apparatus (mobile imaging apparatus 50) according to a second embodiment of the present invention will be described. FIG. 6 is a diagram illustrating a configuration of the mobile imaging apparatus 50 according to the second embodiment. The first embodiment has described the configuration using the receiving unit 36 in order to receive the information for recognizing the switching area for switching between wireless and wired communication. The present embodiment will describe a configuration in which position information (current position) of the mobile imaging apparatus 50 is obtained as the information for switching between wireless and wired communication. Note that the same reference numerals are given to the same constituent components as those in the first embodiment, and descriptions thereof are omitted.

The mobile imaging apparatus 50 includes, in the main body 21 thereof, a current position recognition unit 51 for obtaining a current position (position information) of the mobile imaging apparatus 50 within a hospital (within facilities), and the current position recognition unit 51 successively transmits the obtained position information to the control unit 32. Detection units 52 and 53, together with the detection unit 25, detect position information of the mobile imaging apparatus 50 in the areas in which it can move. The current position recognition unit 51 calculates the relative positional change of the mobile imaging apparatus 50 based on information from the detection unit 25 that detects the rotation of wheels 24 of the mobile imaging apparatus 50, the detection unit 52 that detects the moving direction of the mobile imaging apparatus 50, and the detection unit 53 that detects the movement in the gravitational direction (vertical direction, i.e., the y direction in FIG. 6). Here, the detection unit 53 detects the movement in the gravitational direction (vertical direction) when the mobile imaging apparatus 50 has moved to a different floor in the hospital. Then, the current position recognition unit 51 obtains, from this calculation result, the current position information of the mobile imaging apparatus 50.

The calculation unit of the control unit 32 obtains information by comparing the detected position information with map information indicating a layout of areas in which the moving unit can move. Then, the calculation unit of the control unit 32 obtains, based on the comparison result, information indicating whether the moving unit of the mobile imaging apparatus 50 is located in the wired communication area, the wirelessly communicable area, or the switching area for switching between wireless and wired communication.

Figure 7:
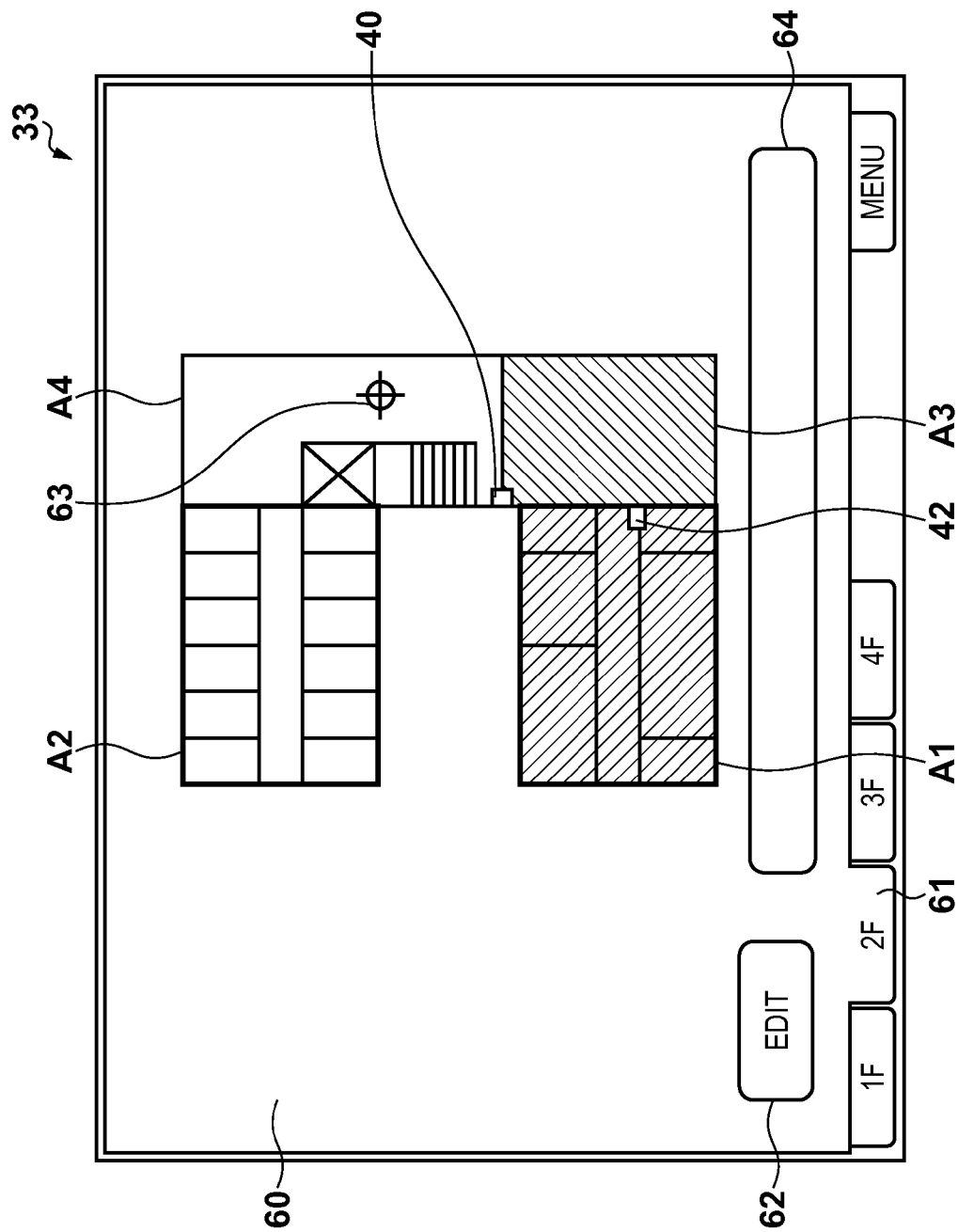
FIG. 7 is a diagram illustrating exemplified monitor display of the second embodiment.

On the other hand, the input and output unit 33 arranged in the upper portion of the main body 21 is constituted by a monitor (display unit) for display output, and an input device for inputting an operation of the mobile imaging apparatus 50. The map information indicating a layout of the areas in the hospital in which the moving unit of the mobile imaging apparatus 50 can move is stored in the storage unit of the control unit 32. The monitor (display unit) 60 of the input and output unit 33 has a function to display a layout in the hospital based on the map information as shown in FIG. 7. The map information is generated for each floor in the hospital, and a user can switch the display to the layout of the floor to be displayed with the use of a tub 61 and check the layout. The monitor (display unit) 60 also has a function to input and edit the information for switching between wireless and wired communication on the communication management level, and the user can press an editing button 62 to shift the mode to an input mode or an editing mode.

As shown in FIG. 7, the monitor (display unit) 60 displays the area A2 (wireless communication area) in which wireless communication is possible for imaging during a doctor's round, the area A1 (wired communication area) in which wireless communication should be restricted during a doctor's round, and the area A3 (wireless/wired switching area) between the area A1 and the area A2. The user can press the editing button 62 in the input and editing modes and set identification display so as to easily visually recognize each area. For example, the identification display in the input mode and the editing mode can be set so as to display the area A1 (wired communication area) and the area A3 (wireless/wired switching area) with hatching as shown in FIG. 7. Also, color display in the input mode and the editing mode can be set so as to display the areas in different colors, in order to obtain a more visual depiction.

The monitor (display unit) 60 also displays a marker 63 indicating the current position of the mobile imaging apparatus 50, and the user can visually recognize the relative positional relationship between the mobile imaging apparatus 50 and the areas. Further, a space 64 for displaying a message for giving an instruction to the operator (technician) is provided on the monitor (display unit) 60. An area information indicating in which area the moving mobile imaging apparatus 50 is currently located (for example, the area A1, A2, or A3), and a message for informing the operator of approach of the apparatus to the wired communication area and for instructing him or her to switch to wired communication are displayed in the space 64 as character information. Such functions helps the operator's recognition and makes the operator reliably perform the switching operation to the wired communication, thereby making it possible to prevent the occurrence of troubles caused by the switching operation being forgot and wireless communication being performed in the wired communication area.

According to the above-described embodiment, it is possible to switch communication with the imaging unit based on the information indicating in which area the mobile imaging apparatus is located, among the wired communication area, the wirelessly communicable area, and the switching area for switching between wireless and wired communication.

It is therefore possible to comply with the restriction of wireless communication without the operator being conscious of it, and to suppress the effect of the wireless communication on other devices within a hospital.

Also, it is possible to use the imaging unit (electronic cassette) in the highly reliable and secure state by managing the communication system of the imaging unit such that wireless communication is switched to wired communication using a cable when the imaging unit moves from the wirelessly communicable area to the wired communication area.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blue-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-051136, filed Mar. 14, 2013, which is hereby incorporated by reference herein in its entirety.

What is claimed is:

1. A mobile radiation imaging apparatus comprising:
an irradiation unit configured to emit radiation;
a main body of the mobile radiation imaging apparatus;
a moving unit configured to move the main body of the mobile radiation imaging apparatus with the irradiation unit; and
an imaging unit configured to take an image of an object irradiated with radiation and capable of transmitting the image to the main body via wireless communication or wired communication,
wherein the main body comprises:
a wireless communication unit configured to communicate with the imaging unit via the wireless communication;
an obtaining unit configured to obtain information by receiving a signal that is transmitted from a first external transmitting unit and indicates a boundary between a wireless prohibited area and a switching area located between the wireless prohibited area and a wireless communication area, and a signal that is transmitted from a second external transmitting unit that is different from the first transmitting unit and indicates a boundary between the wireless communication area and the switching area; and
an instructing unit configured to instruct an operator to switch between wired communication and wireless communication in a case in which the obtaining unit obtains information indicating that the mobile radiation imaging apparatus is at the switching area.

2. The apparatus according to claim 1, further comprising a control unit configured to switch the communication with the imaging unit depending on the obtained information.

3. The apparatus according to claim 2, wherein the control unit is configured to receive the image transmitted from the imaging unit via the wireless communication when the moving unit is located in the wireless communication area.

4. The apparatus according to claim 2, wherein the control unit is configured to restrict the wireless communication with the imaging unit when the moving unit is located in the wireless prohibited area.

5. The apparatus according to claim 1, wherein the obtaining unit is configured to obtain the information indicating that the mobile radiation imaging apparatus is at the switching area located between the wireless communication area in which the wireless communication is possible between the imaging unit and the main body and the wireless prohibited area in which the wireless communication is possible between the imaging unit and the main body but the wireless communication is restricted.

6. The apparatus according to claim 1, further comprising a detection unit configured to detect position information indicating a position of the mobile radiation imaging apparatus, wherein the obtaining unit is configured to obtain the information by comparing the position information with map information indicating a layout of the areas in which the moving unit can move.

7. The apparatus according to claim 6, further comprising a display unit configured to display a relative position of the moving unit in the areas in which the moving unit can move based on the result of the comparison between the position information and the map information.

8. The apparatus according to claim 7, wherein the instructing unit is configured to instruct the operator to switch between the wireless communication and the wired communication by displaying, on the display unit, a message to switch between the wireless communication and the wired communication, or alerting the operator by sound to switch between the wireless communication and the wired communication.

9. The apparatus according to claim 2, wherein the control unit is configured to determine from the obtained information whether the moving unit is moving from the wireless prohibited area to the switching area or from the wireless communication area to the switching area, and to, in a case in which the moving unit is moving from the wireless communication area to the switching area, if the switching from the wireless communication to the wired communication is not performed, increase an operation load needed for the movement of the moving unit.

10. A method for controlling a mobile radiation imaging apparatus that includes an irradiation unit configured to emit radiation, a main body of the mobile radiation imaging apparatus, a moving unit configured to move the main body of the mobile radiation imaging apparatus with the irradiation unit, an imaging unit configured to take an image of an object irradiated with radiation and is capable of transmitting the image to the main body via wireless communication or wired communication, and a wireless communication unit configured to communicate with the imaging unit via the wireless communication, the method comprising:
a communicating step of communicating with the imaging unit using the wireless communication unit;
an obtaining step of obtaining information by receiving a signal that is transmitted from a first external transmitting unit and indicates a boundary between a wireless prohibited area and a switching area located between the wireless prohibited area and a wireless communication area, and a signal that is transmitted from a second external transmitting unit that is different from the first transmitting unit and indicates a boundary between the wireless communication area and the switching area; and
an instructing step of instructing an operator to switch between wired communication and wireless communication in a case in which, in the obtaining step, information has been obtained indicating that the mobile radiation imaging apparatus is at the switching area.

11. A non-transitory computer-readable storage medium storing therein computer executable instructions for causing a computer to execute the steps of the method for controlling a mobile radiation imaging apparatus that includes an irradiation unit configured to emit radiation, a main body of the mobile radiation imaging apparatus, a moving unit configured to move the main body of the mobile radiation imaging apparatus with the irradiation unit, an imaging unit configured to take an image of an object irradiated with radiation and is capable of transmitting the image to the main body via wireless communication or wired communication, and a wireless communication unit configured to communicate with the imaging unit via the wireless communication, the method comprising:
a communicating step of communicating with the imaging unit using the wireless communication unit;
an obtaining step of obtaining information by receiving a signal that is transmitted from a first external transmitting unit and indicates a boundary between a wireless prohibited area and a switching area located between the wireless prohibited area and a wireless communication area, and a signal that is transmitted from a second external transmitting unit that is different from the first transmitting unit and indicates a boundary between the wireless communication area and the switching area; and
an instructing step of instructing an operator to switch between wired communication and wireless communication in a case in which, in the obtaining step, information has been obtained indicating that the mobile radiation imaging apparatus is at the switching area.

12. A mobile radiation imaging apparatus comprising:
an irradiation unit configured to emit radiation;
a main body of the mobile radiation imaging apparatus; and
a moving unit configured to move the main body of the mobile radiation imaging apparatus with the irradiation unit, and an imaging unit that is configured to take an image of an object irradiated with radiation and that has a communication unit capable of transmitting the image to the main body via wireless communication or wired communication,
wherein the main body comprises:
a wireless communication unit configured to communicate with the communication unit arranged in the imaging unit; and
an obtaining unit configured to obtain information by receiving a signal that is transmitted from a first external transmitting unit and indicates a boundary between a wireless prohibited area and a switching area located between the wireless prohibited area and a wireless communication area, and a signal that is transmitted from a second external transmitting unit that is different from the first transmitting unit and indicates a boundary between the wireless communication area and the switching area.

13. The apparatus according to claim 1, wherein the obtaining unit is configured to obtain information indicating that a position of the mobile radiation imaging apparatus is at the switching area for switching between the wireless communication area and the wireless prohibited area.

14. The apparatus according to claim 13, wherein the instructing unit is configured to instruct an operator to switch from wireless communication to wired communication for the imaging unit in a case in which the obtaining unit obtains information indicating that the position of the mobile radiation imaging apparatus has moved from the wireless communication area to the wireless prohibited area via the switching area.

15. A mobile radiation imaging apparatus comprising:
an irradiation unit configured to emit radiation;
a main body of the mobile radiation imaging apparatus;
a moving unit configured to move the main body of the mobile radiation imaging apparatus with the irradiation unit; and an imaging unit configured to take an image of an object irradiated with radiation and capable of transmitting the image to the main body via wireless communication or wired communication, wherein the main body comprises:
- a wireless communication unit configured to communicate with the imaging unit via the wireless communication; and
- a control unit configured to determine from information whether the moving unit is moving from a wireless communication area to a switching area between the wireless communication area and a wireless prohibited area, and, in a case in which the moving unit is moving from the wireless communication area to the switching area, increase an operation load needed for the movement of the moving unit.

16. A method for controlling a mobile radiation imaging apparatus that includes an irradiation unit configured to emit radiation, a main body of the mobile radiation imaging apparatus, a moving unit configured to move the main body of the mobile radiation imaging apparatus with the irradiation unit, an imaging unit configured to take an image of an object irradiated with radiation and is capable of transmitting the image to the main body via wireless communication or wired communication, and a wireless communication unit configured to communicate with the imaging unit via the wireless communication, the method comprising:
- a communicating step of communicating with the imaging unit using the wireless communication unit; and
- a controlling step of determining from information whether the moving unit is moving from a wireless communication area to a switching area between the wireless communication area and a wireless prohibited area, and, in a case in which the moving unit is moving from the wireless communication area to the switching area, increasing an operation load needed for the movement of the moving unit.

17. A non-transitory computer-readable storage medium storing therein computer executable instructions for causing a computer to execute the steps of the method for controlling a mobile radiation imaging apparatus that includes an irradiation unit configured to emit radiation, a main body of the mobile radiation imaging apparatus, a moving unit configured to move the main body of the mobile radiation imaging apparatus with the irradiation unit, an imaging unit configured to take an image of an object irradiated with radiation and is capable of transmitting the image to the main body via wireless communication or wired communication, and a wireless communication unit configured to communicate with the imaging unit via the wireless communication, the method comprising:
- a communicating step of communicating with the imaging unit using the wireless communication unit; and
- a controlling step of determining from information whether the moving unit is moving from a wireless communication area to a switching area between the wireless communication area and a wireless prohibited area, and, in a case in which the moving unit is moving from the wireless communication area to the switching area, increasing an operation load needed for the movement of the moving unit.

* * * * *